United States Patent
Apostolos et al.

(10) Patent No.: US 8,922,211 B2
(45) Date of Patent: Dec. 30, 2014

(54) METHOD AND APPARATUS FOR SENSING THE PRESENCE OF EXPLOSIVES, CONTRABAND AND OTHER MOLECULES USING NUCLEAR QUADRUPOLE RESONANCE AND A SWEPT FREQUENCY CONTINUOUS WAVE SOURCE

(75) Inventors: John T. Apostolos, Lyndeborough, NH (US); Paul A. Zank, Brookline, NH (US); Judy Feng, Nashua, NH (US)

(73) Assignee: BAE Systems Information and Electronic Systems Integration Inc., Nashua, NH (US)

(*) Notice: Subject to any disclaimer, the term of this patent is extended or adjusted under 35 U.S.C. 154(b) by 345 days.

(21) Appl. No.: 13/369,510

(22) Filed: Feb. 9, 2012

(65) Prior Publication Data
US 2012/0206141 A1    Aug. 16, 2012

Related U.S. Application Data

(60) Provisional application No. 61/441,671, filed on Feb. 11, 2011.

(51) Int. Cl.
| | |
|---|---|
| *G01N 24/08* | (2006.01) |
| *G01R 33/44* | (2006.01) |
| *G01R 33/3815* | (2006.01) |
| *G01V 3/00* | (2006.01) |

(52) U.S. Cl.
CPC ............ *G01N 24/084* (2013.01); *G01R 33/441* (2013.01)
USPC ............ 324/309; 324/307; 324/318; 702/23; 600/409; 340/539.26

(58) Field of Classification Search
CPC ............ G01R 33/441; G01R 33/3607; G01R 33/3804
USPC .................................................. 324/300–322
See application file for complete search history.

(56) References Cited

U.S. PATENT DOCUMENTS

| | | | |
|---|---|---|---|
| 5,804,967 A * | 9/1998 | Miller et al. ................... | 324/314 |
| 6,597,185 B1 | 7/2003 | Talanov et al. | |
| 7,188,513 B2 * | 3/2007 | Wilson ......................... | 73/31.05 |
| 2003/0071619 A1 | 4/2003 | Sauer et al. | |
| 2004/0222790 A1 * | 11/2004 | Karmi et al. ................... | 324/300 |
| 2005/0017751 A1 | 1/2005 | Gunn et al. | |
| 2006/0122484 A1 * | 6/2006 | Itozaki et al. ................. | 600/409 |
| 2006/0261942 A1 * | 11/2006 | Frank ....................... | 340/539.26 |
| 2007/0266771 A1 | 11/2007 | Goldson et al. | |
| 2008/0018332 A1 * | 1/2008 | Lieblich et al. ................ | 324/300 |
| 2008/0036462 A1 * | 2/2008 | Schiano ......................... | 324/318 |
| 2009/0091491 A1 | 4/2009 | Ujita et al. | |
| 2009/0234204 A1 | 9/2009 | Ridder et al. | |
| 2012/0086450 A1 * | 4/2012 | Crowley et al. ............... | 324/315 |

* cited by examiner

*Primary Examiner* — Melissa Koval
*Assistant Examiner* — Emily Chan
(74) *Attorney, Agent, or Firm* — Hayes Soloway PC; Todd A. Sullivan; Daniel J. Long

(57) ABSTRACT

Stimulated emissions due to nuclear quadropole resonance are detected utilizing a terminated balanced transmission line and a directional coupler for the detection of explosives, contraband, narcotics and the like that exist between the transmission lines, in which a swept frequency continuous wave generator is utilized to scan between 100 KHz and 10 MHz.

27 Claims, 11 Drawing Sheets

METHOD AND APPARATUS FOR SENSING THE PRESENCE OF EXPLOSIVES, CONTRABAND AND OTHER MOLECULES USING NUCLEAR QUADRUPOLE RESONANCE AND A SWEPT FREQUENCY CONTINUOUS WAVE SOURCE

RELATED APPLICATIONS

This Application claims rights under 35 USC §119(e) from U.S. Application Ser. No. 61/441,671 filed Feb. 11, 2011, the contents of which are incorporated herein by reference.

FIELD OF THE INVENTION

This invention relates to the use of nuclear quadrupole resonance for the detection of molecules and more particularly to the use of a swept frequency continuous wave signal and balanced transmission lines as a sensor to detect molecules such as explosives, narcotics and other molecules of interest, for instance at airports, subways, buildings and shipping containers.

BACKGROUND OF THE INVENTION

As described in U.S. patent application Ser. No. 12/957,843, filed Dec. 1, 2010, in the early 1900s, not long after Einstein published his equations on thermal equilibrium, individuals realized that there were likely to be resonances at very low frequencies for atoms and molecules and that these resonances would occur because if one emits a photon of exactly the correct frequency, the material will absorb this photon, store it for some amount of time and then get rid of the absorbed energy. It is has been found that in nature the molecules which absorb such energy always fall to a lower energy state.

One of the ways for the material to emit energy is through spontaneous emission where a photon of exactly the same energy that is impinging on the material is thrown off in a random direction at random times.

The second way of getting rid of the energy absorbed by the material is through process of stimulated emission in which a photon arrives at exactly the appropriate energy, gets near the molecule, stimulates the molecule and when the molecule drops to the lower energy state it emits a photon that is exactly in phase with the original photon.

The energy that is thrown off either in spontaneous emission or stimulated emission results in an exceedingly narrow spectral line. In fact the line is generally considered to be a single line that exists at a given wavelength or frequency. It is noted that the material only has one choice assuming that the material is pumped at its lowest energy state, raising the energy within the molecule such that the only way that it can release its energy is to emit a photon of that exact energy.

Nuclear quadrupole resonance has been utilized in the past to detect the presence of specific molecules, including explosives. Explosives generally involve the use of nitrogen or nitrogen bonded with other elements. When nuclear quadrupole resonance was utilized in the past, it was used to detect the presence of molecules due to the molecular elements that are bonded together such that the molecules absorb energy at for instance as many as eight different energy levels or spectral lines. It turns out that at least three of the energy levels tend to be prominent, although in some materials there are upwards of all eight energy levels for one bond. If one has many bonds there may be many dozens of spectral lines. In order to detect the presence of a molecule one usually is looking to pump energy right at the top of one of the spectral lines and look for energy coming back at the same frequency.

It has been found that the spectral lines of interest especially for explosives are in the 100 KHz to 10 MHz range. A particularly interesting explosive is called RDX which has a spectral line in the 3 to 4 MHz range, as does sodium nitrate.

However if one is seeking to detect stimulated or emission or spontaneous emission at 3 MHz, the wavelength of the returns is incredibly long, in some cases corresponding to the size of a building. Moreover, the photons that are emitted in either spontaneous or stimulated emission represent very little energy. For instance, a red photon carries an energy of about 3.5 electron volts, with detectable radiation being one or two millionths of 3.5 electron volts. The result is that photons emitted from the molecules are virtually undetectable. One of the reasons is that in order to detect single photons one is faced with thermal background that overwhelms the detection process. In order to achieve any type of result, one pumps large numbers of photons into the target material such that for every milliwatt second an extraordinary number of photons are involved.

If the photons are at the appropriate frequency they are absorbed and only when the frequency exactly corresponds to a resonance line does the molecule start absorbing the photons. It was thought that the frequency source utilized in the nuclear quadrupole resonance measurements needed to be extremely precise and stable. Moreover, it has now been found that one may use a swept frequency continuous wave source.

SUMMARY OF INVENTION

Rather than using the high power noise-prone pulsed coil system for detecting nuclear quadrupole resonance lines due to spontaneous emission, in the subject system stimulated emission is sensed. For stimulated emissions, the energy produced by the molecule is not spontaneous and it is not happening randomly. Rather, the emission that is seen in the stimulated emission is coming back exactly in phase with the incident radiation, namely a coherent response.

In the subject system a low power swept frequency continuous wave source is used in combination with a probe in the form of a terminated balanced transmission line in which molecules including explosives, narcotics and the like that are located between the transmission line elements are detected. In the subject system the result of the absorption of the milliwatt/watt energy is picked off as the frequency is swept with a directional coupler or circulator so as to eliminate the transmitted energy from swamping the received energy. What is seen is the 1% stimulated emission coherent result that is exactly in-phase with the transmitted signal at the instant that the sweep lands directly on an absorption or spectral line. It is the coherent in-phase relationship that permits integrating the weak signals into a detectable result.

As a result of utilizing the directional coupler the transmitted signal is rejected. Moreover, the utilization of a balanced transmission line permits the frequency sweeping because it is not resonant at any frequency since the transmission line is not resonant at any one frequency, a sample can be frequency swept with signals across a band that includes spectral lines for instance between 100 KHZ and 10 MHZ. Moreover a balanced transmission line essentially has a zero Q, thus eliminating the background noise associated with the high Q coils, In one embodiment, the energy is not step wise swept lines. Rather in the subject invention there is a continuous frequency sweep with the dwell at a given spectral line being sufficient to obtain detection.

The subject system in one embodiment is operated at 1.7 watts. In this embodiment, it has been found that there is sufficient dwell time at 1.7 watts to detect simulated emissions, making the system much safer than the high power kilowatt pulsed coil nuclear quadrupole resonance systems. Moreover, quenching is unnecessary.

For robust detection of the stimulated emission, more than one spectral line can be considered as an indicator of the molecule. For instance, for RDX one might wish to detect returns at two or three of the RDX spectral lines. If it turns out that glycine is present, and if in fact one of the RDX spectral lines share a spectral line with the glycine, then one could ignore the overlapping spectral line.

It is also possible to use a pseudo-random number code pattern so that the system would be difficult to jam. Moreover, the low power system is hard to detect, obscuring the fact that any scanning is going on at all.

Note in the subject system that no single detection of a spectral line is used to declare the presence of the target material. Rather, the system desirably requires multiple hits in order to declare the presence of the target material.

It is also noted that the subject system looks at the stimulated emissions, as opposed to the spontaneous emissions, primarily because the spontaneous emissions are perhaps one two millionth of the power of the stimulated emissions. This is important because, as mentioned above, in determining the presence of a target molecule, one is seeing only 1% of the incident energy being returned.

Further, RDX resonances have a bandwidth of approximately 400 hertz which results in a decay time or relaxation time of about 2.5 milliseconds. Assuming a swept frequencies approach, the nucleus of the atoms making up the molecules are excited and when they go into the upper state, there is a population inversion in these nuclei, with the stimulated emission occurring immediately thereafter. Note that the stimulated atoms that have been inverted relax coherently such that there is a coherent response back to the probe. Because of the 2.5 millisecond relation time sweep timing speed is adjusted to provide sufficient dwell time, in one embodiment 1 to 5 milliseconds.

With a flux density of less than 1 watt per meter$^2$, the signal-to-noise ratio is less for the same integration time. If the flux density is greater than 1 watt per meter$^2$, then the signal-to-noise ratio is improved because of the coherent signal. The result of the coherency is that the signal-to-noise ratio improves linearly with how much integration time is utilized.

Integration time refers to the collection of the results of multiple stimulated emissions over time. As a general rule, one has to dwell on the target material for whatever is the inverse of the particular bandwidth involved. Bandwidths in the subject case are on the order of a 100 to 500 hertz which results in dwell times of between 1 and 5 milliseconds.

Since there is no coil involved, one does not have to use quenching and since one uses a directional coupler to ignore the transmitted signal, one does not have to stop and listen in order to get adequate readings. This permits the swept frequency continuous wave source.

Moreover, in one embodiment of the subject invention, a cancellation algorithm is utilized in which the transmission line is observed without a sample between the transmission line elements during a calibration sweep. Thereafter, any material that is between the transmission line elements has results that are subtracted from the calibration sweep results. Thus, if there are any peculiarities in the analyzer or transmission lines, these peculiarities are subtracted out. As a result, steady state noise is nulled out.

The reason for the use of the transmission line is that it focuses all the energy between the two balanced leads or elements. Because a balanced transmission line is the world's worst antenna by design it does not leak energy to the environment, unlike a coil. Concomitantly, the transmission line does not receive interference from the environment, making the subject system an extremely quiet system.

The system is implementable in a number of different forms such as providing two spaced apart transmission line elements to either side of a gate or portal through which an individual is to pass. Such a portal may be an airport security checkpoint. Moreover, two pieces of copper pipe or copper tape may be placed on opposing walls down a corridor to form the transmission line, or the balanced transmission lines can be placed on a road to detect the passage of target material between the transmission line elements. Additionally, the transmission line could for instance be configured as opposed guard rails.

Considering for instance that a terminated balanced line contains two elements, one element is called a plus element and the other is called a minus element. The magnetic flux lines are in a plane perpendicular to the axis of the elements. In one configuration, a large area can be covered using a number of side-by-side plus/minus lines. For instance, these lines could be laid out in a carpet at an airport to track people carrying explosives on their person. Thus, one can monitor the transmission lines to be able to tell where someone carrying explosives is walking and to be able to track their path.

It will be appreciated that the subject system, by avoiding the high Q coil, also avoids the large amount of shielding necessary for public safety or the safety of those operating the equipment. Also, as mentioned above, there is no need to actively quench any part of the probe in order to be able to listen to the relatively small returns from the irradiated sample.

Rather than having to run a kilowatt into a coil, in the subject invention successes have been reported at a 200 milliwatt level with excellent signal to noise ratios. Thus, there is the ability to operate at a 30 dB lower power levels than a pulsed coil. This means that the entire system can be run at low power. The result is that the subject system does not interfere with magnetic media or people's safety and is very hard to detect any distance away from the test site. Thus, even standing a few feet beside the balanced transmission line one is not able to detect it. As a result, a person would not know that he or she is being monitored.

As will be appreciated, the conductors for the transmission lines could be for instance as large as a two inch pipe, or could in fact be flat transmission line elements. It is also noted that the termination resistance is equal to the impedance of the transmission line. In one embodiment, the space between the elements is about 2.5 to 3 feet, such that one could conveniently paint conductive stripes on opposing sides of a corridor, with the impedance being controlled by how tall the stripes are and how far apart the stripes are. For a corridor-sized installation one might have a conductive stripe on either side of the corridor that is 11 feet long and about a foot tall. Also with larger areas one needs more power to create the flux density required. Thus if one considers a 12 foot long probe, this requires about 36 times as much power as a miniature probe. It is the power density (watts/meter^2) that remains constant.

Regardless, one can obtain adequate results in a corridor type situation with between 7 and 10 watts of power into the probe.

The amount of power required is dependant on how much material one is trying to detect and also the flux density that one is trying to excite it with, as well as how much integration time is available.

Small amounts of explosives can be carried on the person in the persons clothing, swallowed, or can even be surgically implanted, which would be virtually undetectable through a physical examination of the person and also through standard X-ray techniques. Thus for the creative or diligent terrorist, it may be of interest to provide pockets of the explosive within the body of the individual that could not be readily detected by present techniques.

It is noted that the maximum flux density given two spaced apart conductors is on a line between the two conductors, with the minimum being outside the transmission line. As one proceeds to the edge of the conductors, one obtains more flux density. However, the flux density does not very significantly in a direction normal to the plane between the two transmission line elements so it is possible to get reasonable coverage for a human sized object or even a truck sized object above the transmission line. Note that the transmission line impedance can typically be between 100 and 1,000 ohms which is not critical. The critical component is the flux density, with the critical flux density being approximately 1 watt per meter$^2$.

As a result, the subject system is capable of detecting an entire class of explosives, whether they are people-born or vehicle-born. Moreover, the subject system may detect contraband such as narcotics, with many narcotics having very specific nuclear quadrupole resonance signatures. This includes cocaine and heroin.

It will be appreciated that for some complex organics the spectral lines tend to be larger, such as those associated with glycine. Glycine, even in its usual 5% concentration for dietary supplements, for instance, can be distinguished by recognizing the glycine spectra and subtracting out the nuclear quadrupole resonance signature. As a result, if it turns out that one of the spectral lines happens to be right on top of the molecule of interest, the subject system provides way to discriminate against the non-target molecules by maintaining returns of a number of spectual lines.

Another application is to be able to detect explosives in shipping containers. In such cases one has an incredibly long integration time available, for instance weeks during which the inspection can take place.

Another different application for the subject technique is in the production of molecular compounds. Explosives for instance have a certain composition which involves a very specific ratio of the molecular components. It has been found that the subject technique can be used to verify the specific percentage ratio of the components in the test sample, so that one can non-destructively inspect materials during production without damaging it.

It has been found that the detected spectral lines are one-to-one correlatable with the ratio of the molecular constituents in a compound so that the measurements are a very accurate prediction of the actual ratio of the elements in the compound.

In summary, stimulated emissions due to nuclear quadrupole resonance are detected utilizing a swept frequency continuous wave source and a terminated balanced transmission line and a directional coupler, thus to detect explosives, contraband, narcotics and the like that exist between the transmission line elements. In one embodiment, the frequency source operates 100 KHz and 10 MHz, with the frequency source being low power so as to not create a safety hazard and so as not to interfere with radiation sensitive devices such as film or electronic circuits that are in the vicinity of the balanced transmission line probe.

BRIEF DESCRIPTION OF THE DRAWINGS

These and other features of the subject invention will be better understood in connection with the Detailed Description, in conjunction with the Drawings, of which.

DETAILED DESCRIPTION

Figure 1:
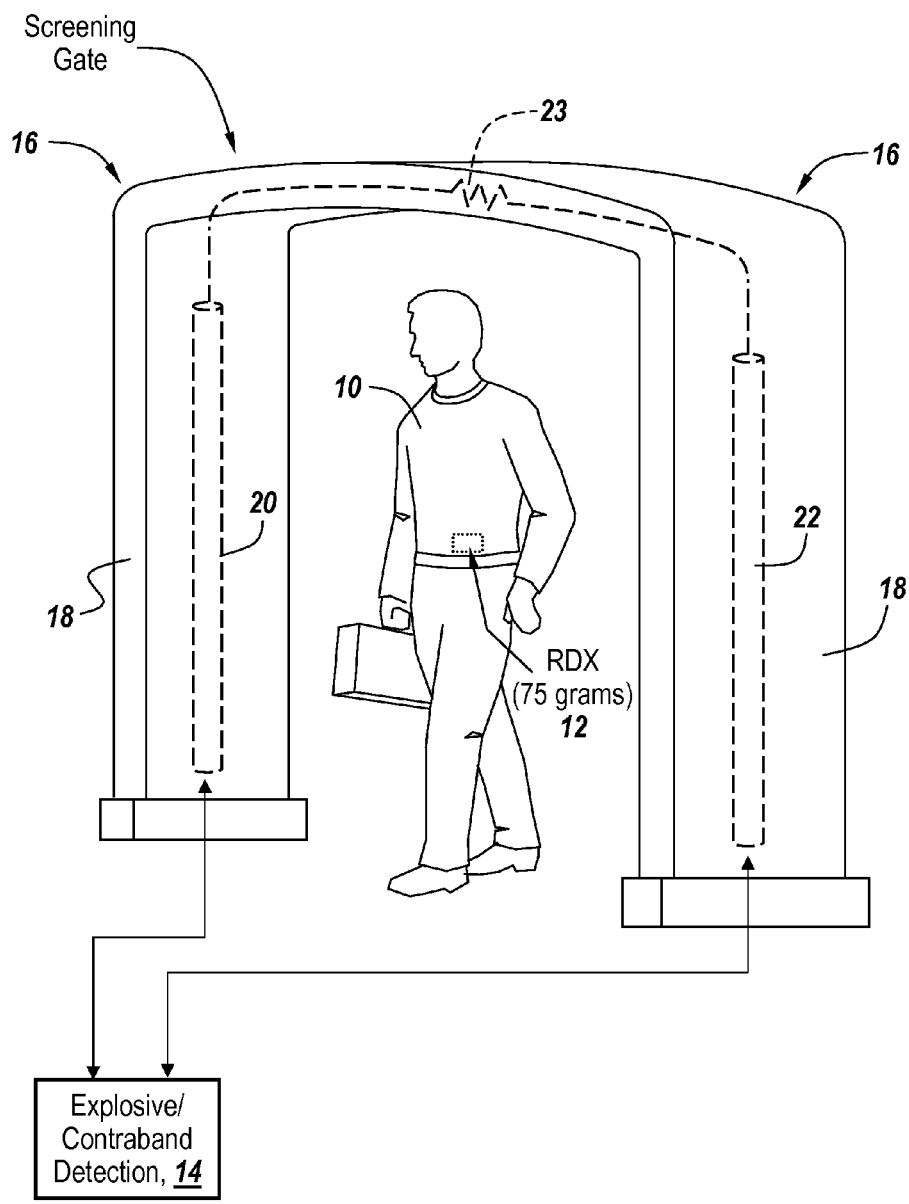
FIG. 1 is a diagrammatic illustration of the detection of an explosive hidden on an individual as the individual walks through a balanced transmission line coupled to an explosive/contraband detection unit that utilizes nuclear quadrupole resonance in which, in one embodiment, RDX spectral lines are detected to ascertain the presence of an explosive.

Prior to describing the subject invention, if one performs a frequency sweep, the emission that comes back is on the order of 1% of the energy that impinges on the molecule.

It is noted that prior nuclear quadrupole resonance techniques can be likened to looking into a headlight to find a 1% response.

As a result, a pulsed coil prior art nuclear quadrupole resonance detection of molecules requires upwards of 100 kilowatts of energy coupled to a very high Q tuned coil having for instance a Q of 80 or better. If there is any offset in terms of the frequency of the incident radiation or if the coil tuning was not precise, then any emissions from the molecule will be lost in the clutter.

First and foremost in the prior art pulsed coil nuclear quadrupole resonance techniques, it was only with difficulty that one could in fact detect any response. One of the reasons is because the coil exhibits a large dwell time after which one looked for a response.

If one did not wait, the incoming radiation would swamp the detectable results. In order to eliminate this problem, those in the past used a pulsed source and then waited for a response after the trailing edge of the pulse. Prior systems thus pumped pulsed energy into a coil with the target material at the center of the coil. Thereafter the material would absorb energy and then the prior systems would listen for the spontaneous decay.

The problem with spontaneous decay is that at thermal equilibrium a spontaneous photon happens only once for every two million stimulated photons. Thus, in terms of detecting spontaneous decay, one is at an extremely difficult power disadvantage. Secondly, the spontaneous decay might happen over several tens of milliseconds which means that the instantaneous power levels at any point in time are very low. For spontaneous decay using a pulsed coil nuclear quadrupole resonance, the problem is that one is working with very few photons and further they are stretched out over time. This means that one has to use huge amounts of power to overcome these problems, often in the nature of kilowatts of energy. Moreover, because one is looking at very low signal strength the coil is made with a very high Q. This means that the coil couples well with the environment, that in turn means that the coil picks up a great deal of background noise.

Pulsed coil nuclear quadrupole resonance detection systems have been marginally cost effective and their power density has exceeded human safe limits.

More specifically, taking RDX as an example, the bandwidth of the RDX resonance is about 400 hertz. This means that the associated decay time or relaxation time is on the order of 2.5 milliseconds. If one were to sweep the frequency through the resonance as one approaches the resonant frequency, what happens is that one excites the nucleus of the nitrogen atom. When the nuclei are excited they go into an upper state and then as one sweeps by the frequency there is a population inversion in these nuclei at which time they start to decay.

If one utilizes a long CW pulse what would happen is that one would see a periodicity of absorption and emission. When the CW pulse is turned on, the molecule goes into the excited state but then relaxes through stimulated emission. What would happen utilizing a CW signal is that one would see a series of absorptions and emissions that would occur every 2.5 milliseconds.

For RDX, assuming a pulsed coil system, one must use a pulse width of about half a millisecond because the pulse has to decay down fast enough so that the spontaneous emission can be observed.

Thus in the past a relatively short pulse of CW energy was used to enable listening for the response. However, in order to be able to detect the response at all, a very high Q coil was required. High Q coils have an excessive relaxation time. As a result, in order to provide for the ability to listen when driving a very high Q coil at half a millisecond one has to have other circuitry to quench the coil as fast as possible so as to be able to listen to the return, typically in terms of a little hiss that comes off after irradiation with the pulse.

Thus, in the prior systems one had to have exceedingly large kilowatt sources of 3 MHz energy in order to obtain enough of a response, and then had to pulse the source so as to be able to stop it and quench it in time to be able to detect the minuscule response that would occur.

Having the high Q coil further was complicated by the fact that one could not frequency sweep a sample because the high Q coil resonates at only one frequency.

This for instance precludes the ability to distinguish between the detection of multiple spectral lines to be able to distinguish the spectral response of the target molecules from the spectral responses from uninteresting molecules.

Also, when using a high Q coil one has to use an exceedingly large amount of shielding to make the system safe for use around people, as well as having to actively quench the coil.

Moreover, when pumping 1 kilowatt into a coil, the presence of the system is very easy to detect. Thus, terrorists could avoid screening knowing that such a detection system was in operation.

Note that the pulsed coil system detects spontaneous not stimulated emissions. Spontaneous emissions are not coherent and one obtains the square root of the power coming back.

Thus, in the past it has been virtually impossible to provide a workable system that would reliably and safely detect dangerous amounts of explosive material hidden on a human.

Referring now to FIG. 1, an individual 10 may be carrying on his or her person some contraband or explosives 12 which may for instance may be secreted in his or her underwear, or could even be surgically implanted. One such explosive is RDX and it is the purpose of the subject invention to be able to detect explosives in as little quantity as 75 grams which is approximately about a fifth of a cup. Terrorists and the like are using more and more sophisticated ways of secreting explosives and/or contraband and a physical examination of the individual may not yield the presence of such explosives or contraband. Not only may the explosives or contraband be surgically implanted in the individual, they may be swallowed in bags and be held internally in the gut until such time as their "removal".

Present systems for detecting such explosives or contraband such as back scatter X-rays are not effective to detect such secreted items and the use of higher power radiation is counterindicated for safety reasons.

On the other hand, as shown in FIG. 1, an explosive or contraband detection system 14 utilizes nuclear quadrupole resonance in which swept frequencies are applied to a balanced and terminated transmission line 16 embedded in a screening gate or housing 18 in which the elements of the balanced transmission line 20 and 21 as well as load 23 are embedded in the gate. The balanced transmission line has no frequency to which it is tuned, such that the application of signals for instance between 100 KHz and MHz may be applied due to the non-tuned nature of the probe which is comprised of elements 20, 21 and 23.

As will be seen, the power necessary to detect nuclear quadrupole resonance is in general below 10 watts and often as little as 200 milliwatts, due to the subject explosives/contraband detection system which, inter alia, utilizes a directional coupler in the form of a circulator to cancel out the transmitted energy while receiving only the stimulated emission from the molecules in the target sample.

As used herein, the target sample 12 includes molecules having a particular recognizable spectrographic signature in which the spectral lines of the sample are recognizable when compared with the spectral lines generated through stimulated emission of all of the remaining molecules that surround the target sample.

For instance, glycine which is common in the human body has spectral lines that are distinguishable for instance from RDX spectral lines, with glycine in essence forming a background spectral signature which is to be distinguished.

While the subject invention will be discussed in terms of explosives, it is understood that the material under test may be molecules of any type having a known spectral signature. This includes contraband such as narcotics and other types of drugs such as heroin and cocaine which, due to the subject system in one embodiment involving stepped and swept frequency transmission enables one to eliminate the spectral signatures of non-target materials while being able to single out the spectra of target materials.

Figure 2:
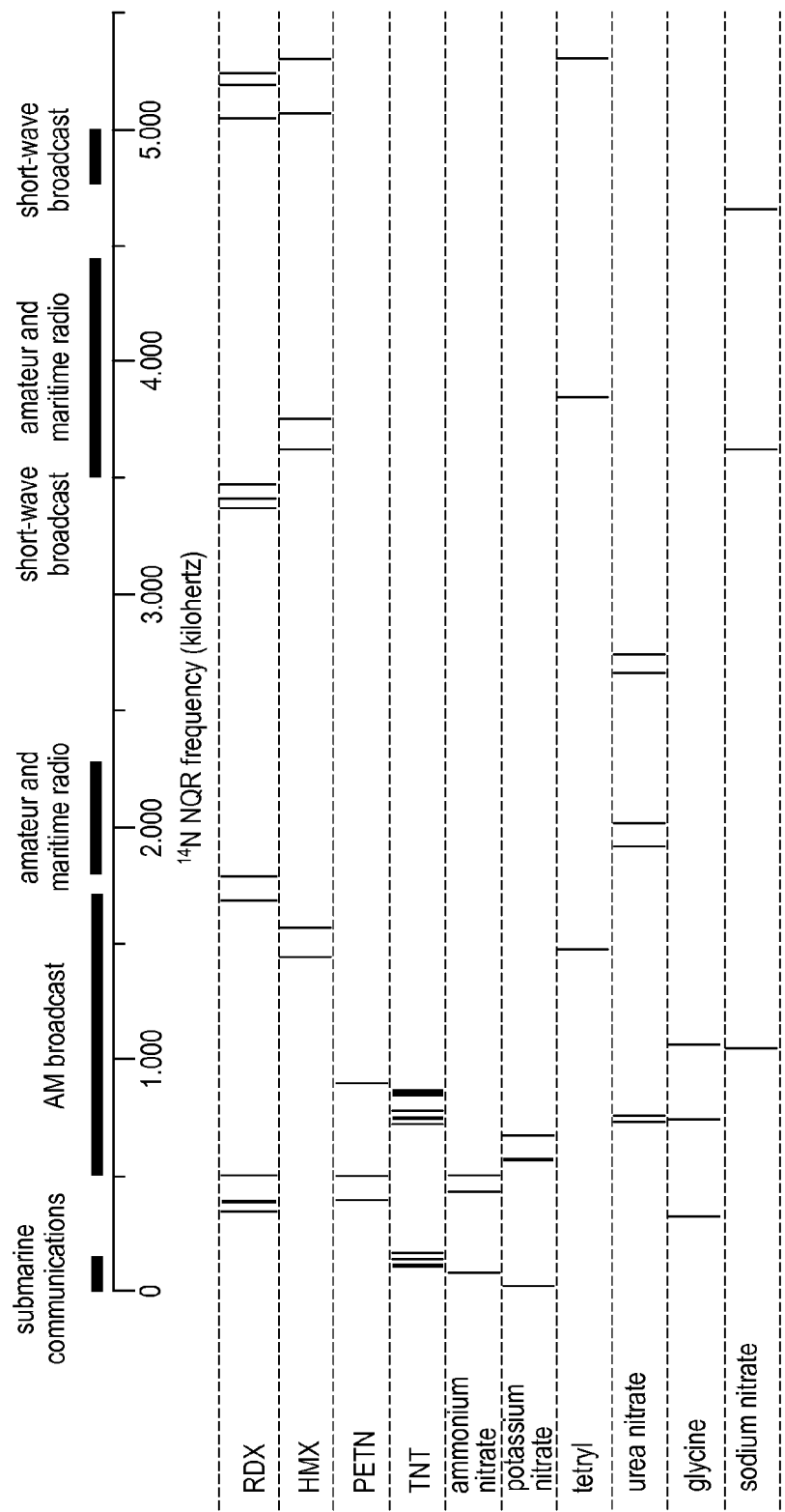
FIG. 2 is a graph showing the spectral signatures of a number of potential explosive materials indicating for RDX and HMX, a spectral signature in a 3-4 MHz range, with TNT indicating a spectral signature in the sub 1 MHz range as well as ammonium nitrate and potassium nitrate, with tetryl having a signature in the 3-4 MHz range and with urea nitrate having a spectral signature not only in the sub 1 MHz range but also in the 2-3 MHz range, noting that sodium nitrate has a very close spectral signature to one of the spectral lines of glycine.

Referring to FIG. 2, what is shown is a spectral chart for common explosive materials such as RDX, HMX, PETN, TNT, ammonium nitrate, potassium nitrate, tetral, urea nitrate and sodium nitrate, also as compared with the spectra of glycine.

What will be seen is that all of these materials have spectra between about 100 KHz and about 5 MHz, which spectra are detectable by the subject system. For instance, if one detects spectra of RDX in the 3-4 MHz band, this is clearly distinguishable from the glycine spectra which lie below 1.5 MHz.

Likewise one can distinguish PETN from RDX as well as being able to distinguish HMX from RDX due to the offset of the spectra of HMX in the 3-4 MHz band from the spectra of RDX.

Since the subject system detects stimulated emission from all of the molecules in the sample between the balanced transmission lines, it is possible through correlation processing to be able to provide a probability of a match between the spectral lines of the target material as opposed to the spectral lines due from molecules that are not target materials and which constitute background.

Figure 3:
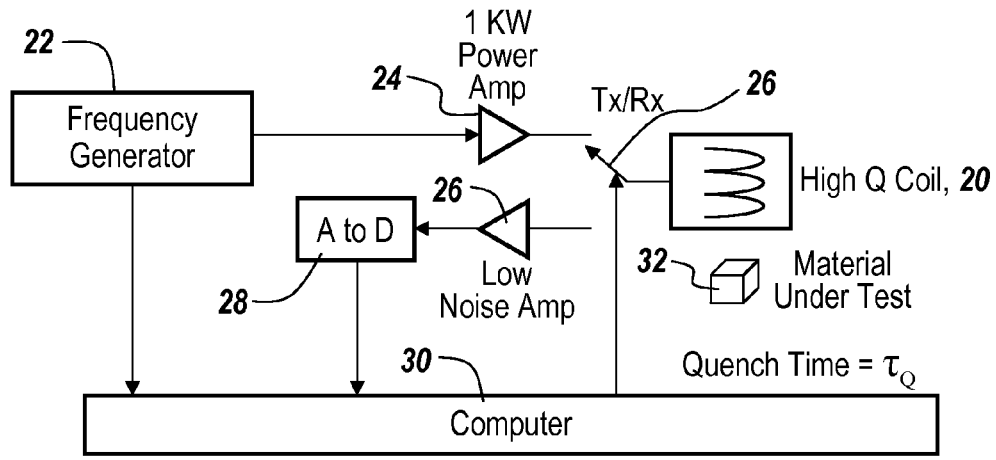
FIG. 3 is a diagrammatic illustration a prior art pulsed coil nuclear quadrupole resonance system illustrating the use of high power pulses and a high Q coil in which the system has a transmit-receive switch, the cycling of which depends on coil quench time.

Referring now to FIG. 3, what will be seen in the prior art pulsed coil nuclear quadrupole resonance system is the utilization of a high Q coil 20 which is driven from a frequency generator 22, the output of which is amplified by an amplifier 24 to the 1 kilowatt level. The signal from the amplifier is switched via a transmit/receive switch 26 and is applied to the coil during a pulsed sequence, with switch 26 being returned to the receive position at which point the high Q coil 20 is coupled to a low noise amplifier 26, to an analog-to-digital converter 28 and thence to a computer 30 for measuring the spontaneous emission response from material under test 32.

In short, since the system described in FIG. 3 measures the spontaneous emission of the material under test and since in order to generate enough spontaneous emission high power was deemed to be necessary, the system of FIG. 3 is clearly not usable around human beings for safety reasons.

Moreover, in order to be able to eliminate the effect of the transmitted power with respect to the relatively low power of the receive signal, it was necessary to be able to quench high Q coil 20 so as to be able to see the return from the material under test. The quench time, $\tau_Q$, is problematic with respect to providing realtime measurements. It has been found that it is important to be able to provide circuitry to be able to quench high Q coil 20 in order to increase the pulse repetition frequency. However, the quench time when utilizing a high Q coil is problematic as mentioned above.

Moreover, the utilization of a high Q coil is problematic because it also collects background, which background can oftentimes obscure the results.

Figure 4:
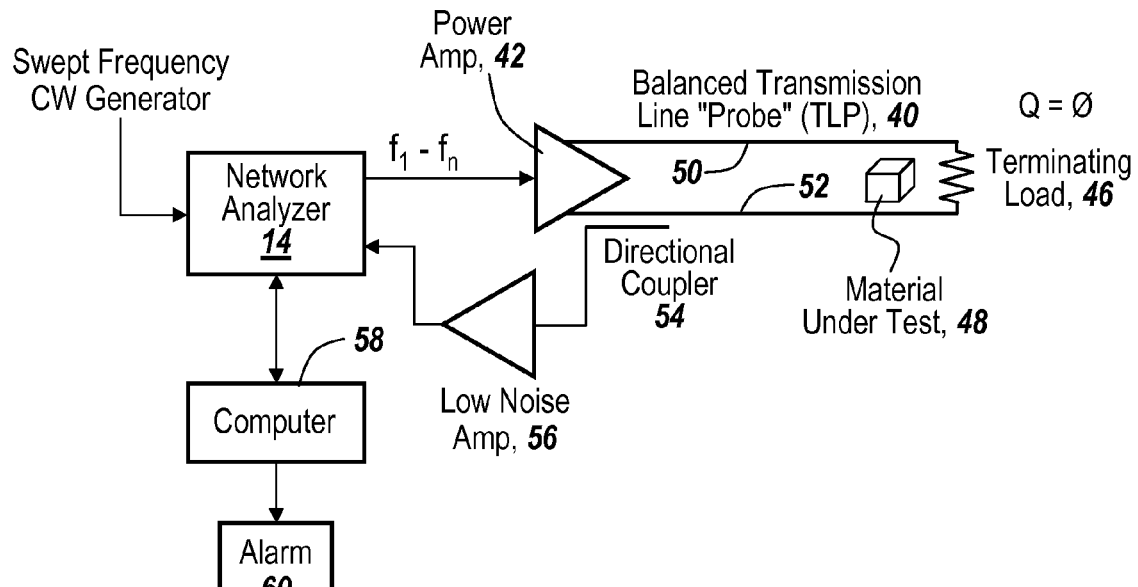
FIG. 4 is a diagrammatic illustration of the subject system illustrating a swept frequency continuous wave source for generating frequency sweep is amplified by a low power amplifier to less than 10 watts in one embodiment, with the amplifier being coupled to a balanced transmission line probe in which the transmission line is terminated in a load and in which a directional coupler is utilized to detect the stimulated emission from a material under test, unimpeded by the output power applied to the transmission line.

On the other hand and referring now to FIG. 4, a balanced transmission line probe 40 is coupled to a power amplifier 42 which amplifies a swept frequency continuous wave generator 44 output. The transmission line is terminated by a terminating load 46.

When a material under test 48 is placed between the balanced transmission line elements 50 and 52, it has been found that the stimulated emission from the material under test can be sensed utilizing a directional coupler 54 coupled to a low noise amplifier 56 which is in turn coupled back to the network analyzer 44 that detects the very low level stimulated response of the material under test. It is noted that network analyzer 44 is coupled to a computer 58 such that the returned signal can be processed and an alarm 60 activated if the material under test has a spectral signature match to that of a target material.

While it is possible to generate only one frequency corresponding to one the major spectral line of the target sample, it is useful to be able to scan frequencies for instance $f_1$-$f_n$ in order to obtain the spectral lines of whatever materials might be between the elements of the balanced transmission line. Because the balanced transmission line has a Q of zero, not only is it possible to couple a wide frequency range of signals to the transmission line, the Q of zero also means that there is very little outside interference with respect to the signals that exist interior to the transmission line.

Moreover it has been found that while the flux densities vary at various positions between the transmission line elements, at least in the plane of the transmission line elements, locating a material under test above or below the plane of the transmission line elements does not materially affect the readings.

Figure 5:
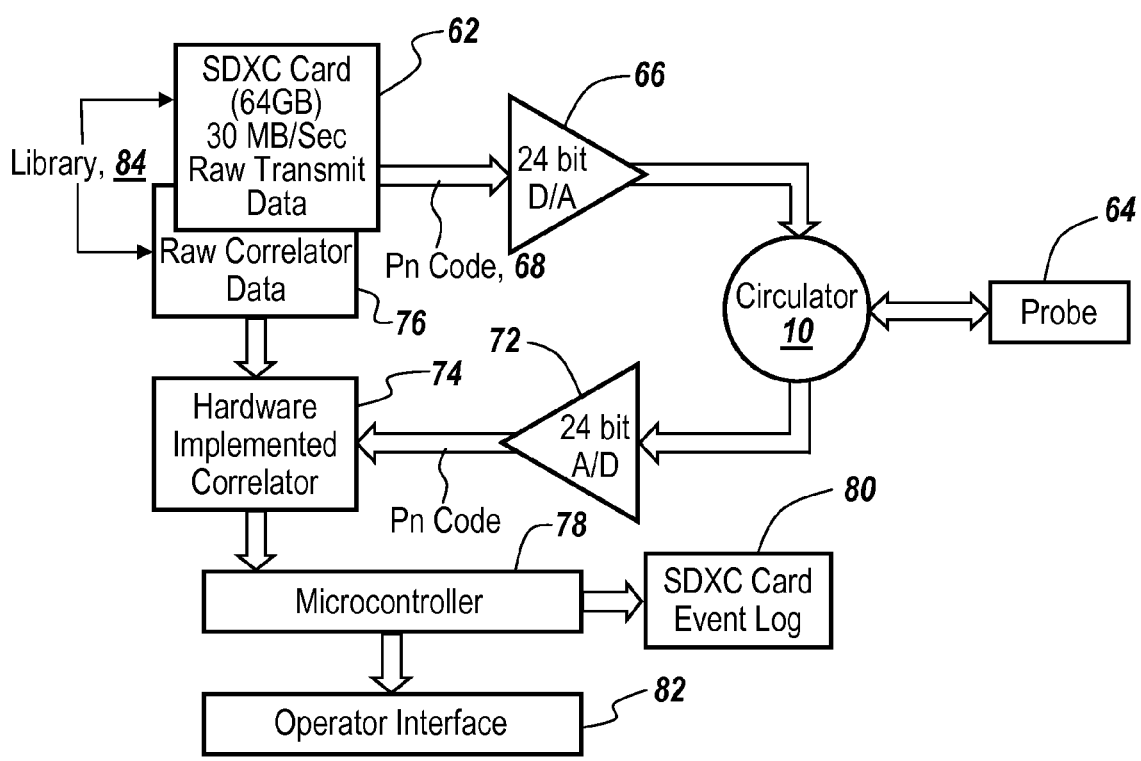
FIG. 5 is a block diagram of the subject system in which transmissions at various swept frequencies are applied through a 24 bit digital-to-analog converter to a circulator that functions as a directional coupler, with the output of the circulator being converted by a 24 bit A-D converter to correlate the returns with raw correlated data from a library, the output of the hardware-implemented correlator provided to a microcontroller for detecting the existence of a particular material present at the probe.

Referring to FIG. 5, in one embodiment an memory card (such as a SXDX 62 gigabyte card) having a 30 MB per second transfer rate may be utilized to generate frequency signals swept from 100 KHz to 10 MHz that are coupled to probe 64 utilizing a 24 bit digital-to-analog converter 66 to which is applied a PN code 68 in one embodiment.

The utilization of a pseudo-random code is for defeating jamming, with the pseudo-random code being similar to that utilized in GPS systems for this purpose.

The input to the probe and the output from the probe are coupled to a circulator 70 which, as described above, completely eliminates the effect of the transmitted signal on the received signal, thereby to eliminate the problems of having to quench a high Q coil.

The output of circulator 70 is applied to a 24 bit analog-to-digital converter 72, with the receive PN code being applied to a hardware implemented correlator 74 that correlates the received stimulated emission information with raw correlator data 76 such that if there is a high correlation between the raw correlator data and the received data, microcontroller 78 may be used to drive memory card event log 80 and also provide an operator interface 82 alarm condition indicator.

Note, a library 84 may be utilized that carries the spectral signatures of many types of target molecules. This results in the ability to analyze a large variety of very narrow frequency signals which are applied to probe 64.

It will be appreciated that the frequency stability of the signal generator in the form of a network analyzer such as shown in FIG. 4 is not critical due to the frequency sweep, since all spectral lines that are generated by the nuclear quadrupole resonance phenomena will be covered.

Figure 6:
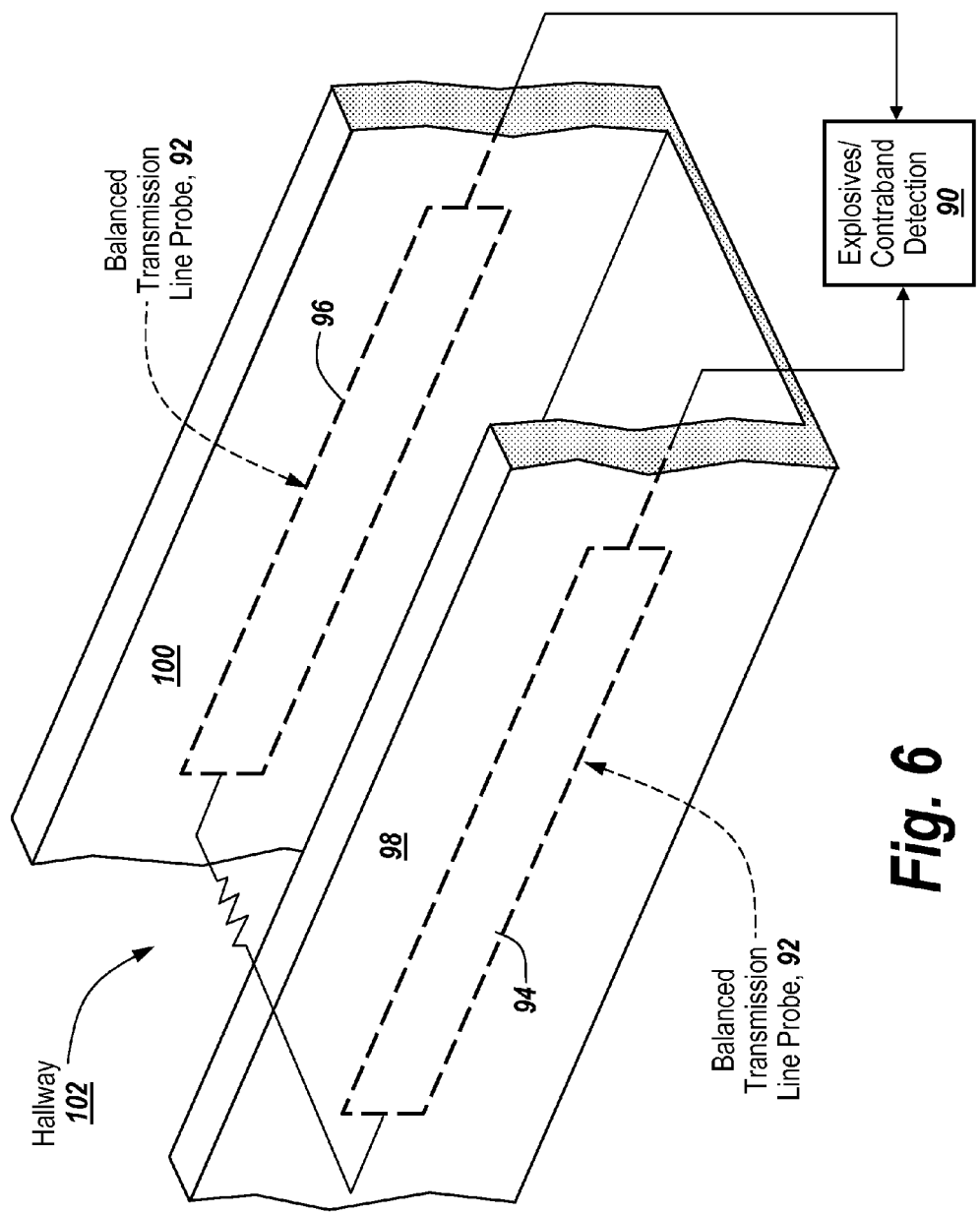
FIG. 6 is a diagrammatic illustration of an embodiment of the subject invention in which explosives detection includes the use of parallel foil strips on opposing walls of a hallway that function as a balanced transmission line probe for detecting target materials carried by a person walking down the hallway.

Referring now to FIG. 6, in one embodiment, an explosive contraband detection system 90 may be coupled to a balanced transmission line probe 92 which includes elements 94 and 96 embedded foil strips in hallway walls 98 and 100, with elements 94 and 96 terminated in a resistance load 102. In this case an entire hallway may be monitored for the presence of target molecules whether carried by a person or in some other conveyance as it transits down a hallway.

Figure 7:
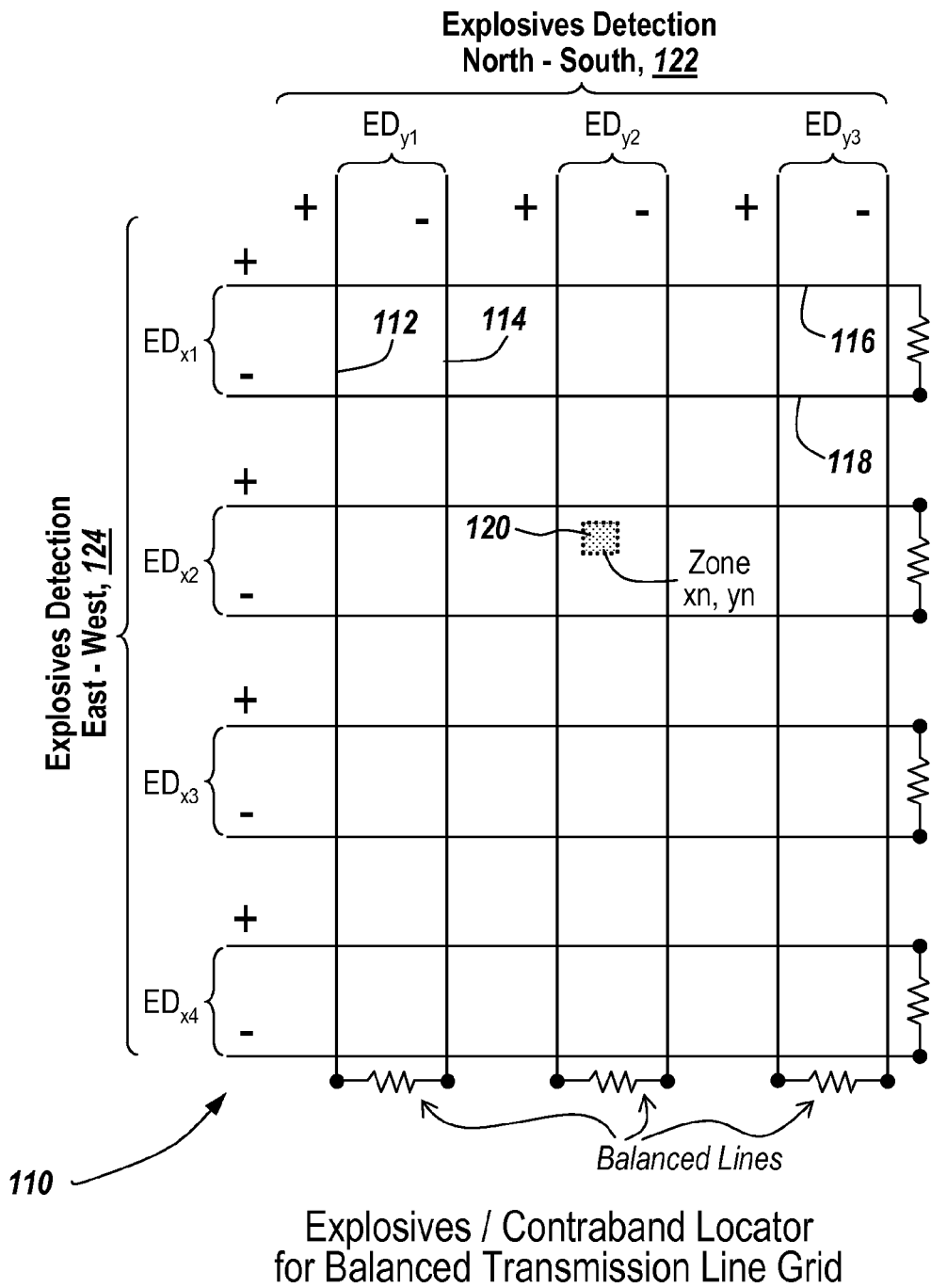
FIG. 7 is a diagrammatic illustration of the utilization of a grid of balanced transmission lines for the location of a target material carried for instance by an individual who traverses the grid.

Referring to FIG. 7, it is possible to provide a grid of balanced transmission lines here shown at 110 to include pairs of transmission lines for instance vertical pairs 112 and 114 indicated by the plus and minus nomenclature for the particular transmission line. Likewise, a crossing or transverse transmission line structure may include transmission lines 116 and 118. By monitoring the results on the various transmission lines one can localize the target molecule as illustrated at 120 as being at position $x_n$, $y_m$. This kind of grid, whether on the floor or surrounding a building can track the presence of explosives or contraband materials and therefore determine the track or path of the individual or conveyance which is transporting these materials.

For this particular embodiment the detection of explosives in for instance the north/south direction here illustrated at 122 is correlated with at explosive detection in east/west direction here illustrated at 124 to provide location.

Figure 8:
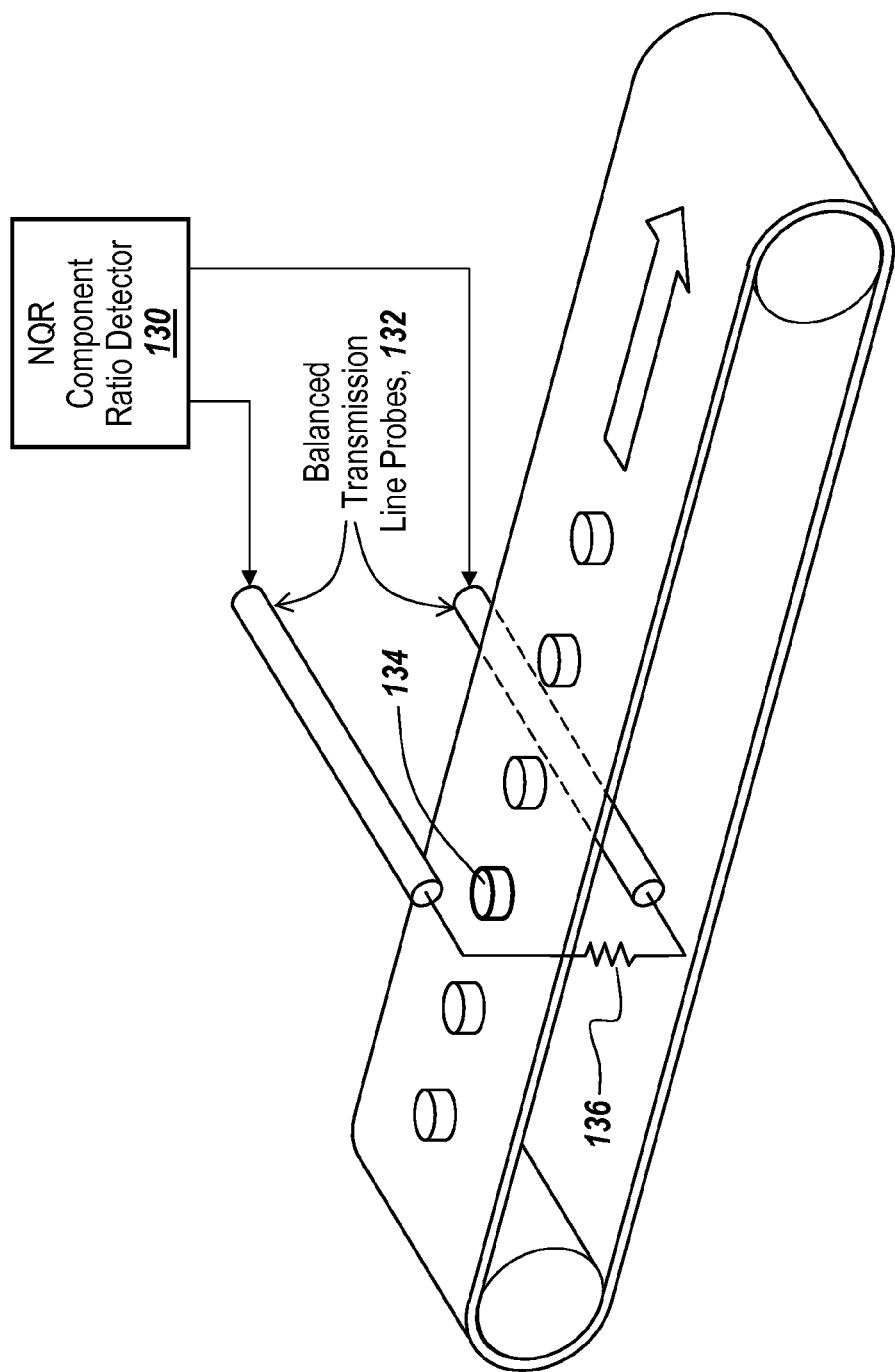
FIG. 8 is a diagrammatic illustration of the use of the subject system as a nuclear quadrupole resonance component ratio detector for detecting the ratio of molecular components in material proceeding down a production line to detect component ratios in a non-destructive environment on the fly as the material passes between the balanced transmission line probe elements.

Referring now to FIG. 8, one of the important characteristics of the subject system is that the molecular component ratio can be detected on the fly in a production line environment to provide non-destructive testing. Here a nuclear quadrupole resonance component ratio detector 130 is utilized with a balanced transmission line probe 132 to, for instance, detect the molecular composition of a drug 134 in pill form as the pills pass through the balanced transmission line probe. It has been found that by sweeping the frequency of the signals to the balanced transmission line probe one can detect not only the spectral lines of the various components in question, but also can detect the ratio of the target components.

Thus, rather than having to perform destructive tests in order to ascertain the constituents of a product being manufactured, one can non-destructively detect the component ratios utilizing the subject nuclear quadrupole resonance system.

Figure 9:
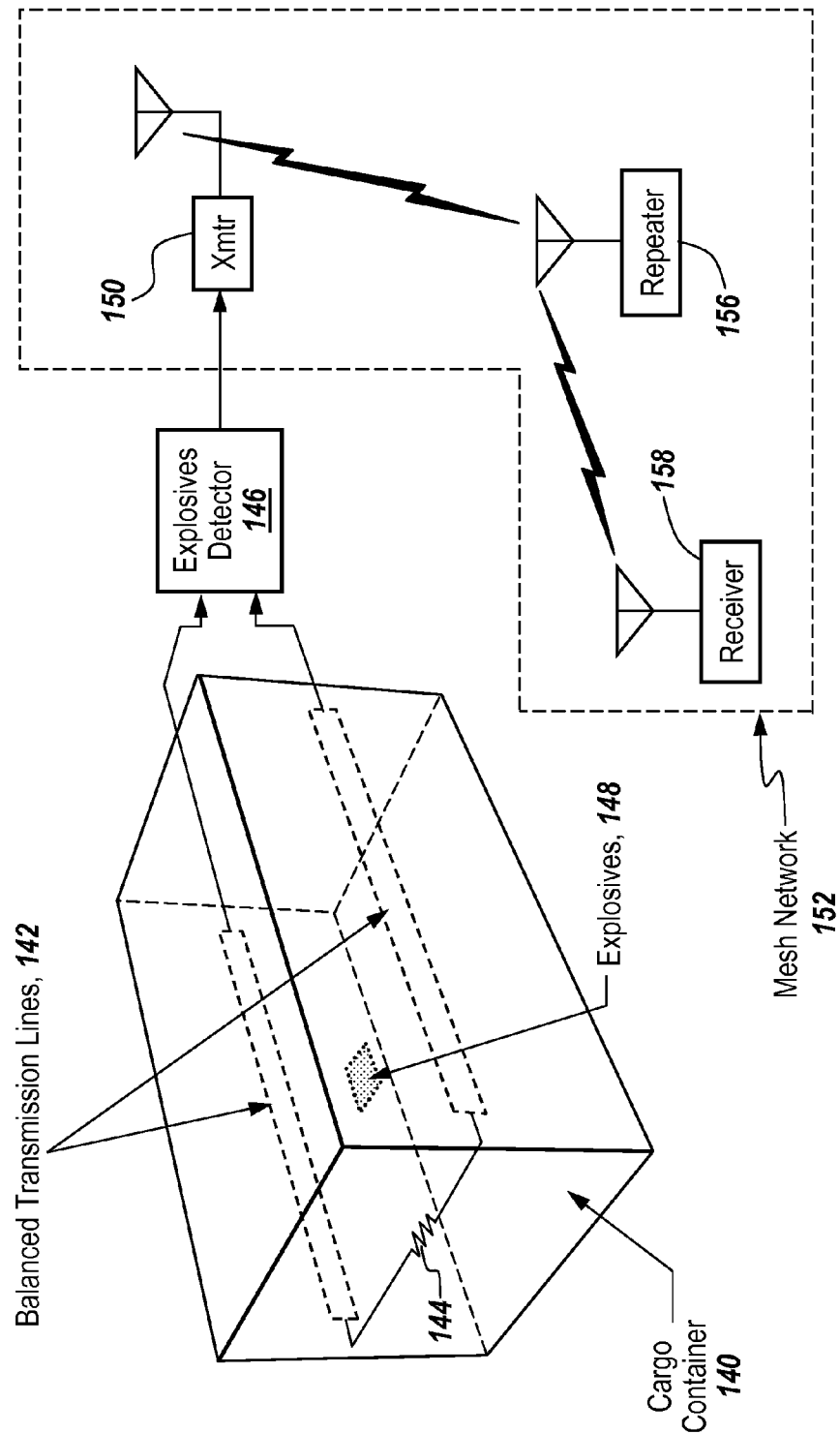
FIG. 9 is a diagrammatic illustration of a shipboard container inspection system utilizing the subject system in combination with a mesh radio network to report incidents to a cargo control room.

Referring to FIG. 9, another embodiment of the subject system is the ability to track the contents of cargo containers that may either be placed shipboard or on other modes of conveyance in which, as illustrated, a cargo container 140 may be provided with internal balanced transmission lines 142 terminated as illustrated at 144 and coupled, for instance, to an explosive detection system 146 of the subject nuclear quadrupole resonance variety. If for instance the containers contain explosives or contraband, here illustrated at 148, whether these materials are initially placed in the container or later clandestinely placed into a sealed container, their presence can be detected as illustrated at 146 by an explosives detector. Through the use of a mesh network 148, the detected results can be communicated from explosives detector 146 and a co-located transmitter 150 which is part of a self establishing mesh network 152 aboard a ship to the cargo control room. Mesh network 152 includes one or more repeaters 156 which relays the information from transmitter 150 to a receiver 158 in the cargo control room.

It is noted that when monitoring containers, due to the length of time on board ship, the integration times available for the sensing of the stimulated emissions are dramatically increased. This long integration time can accommodate lower power detection. What this means is that an exceedingly robust system is available for detecting the relatively minute simulated emissions, with integrating occurring over a long period of time, thanks to the fact that the containers are in transit for substantial periods of time. While this embodiment of the subject system has been described in terms of shipboard containers, any kind of container monitoring on conveyances is within the scope of the subject invention.

It is also possible for instance to utilize the subject system to detect contraband or explosives in trucks that pass through a portal. This is possible due to the relatively thick skin depths associated with metal containers that permit penetration of low frequency signals so that the transmission line carried signals can penetrate well into the containers. Thus, the subject system may be utilized to detect not only person-carried contraband and explosives, but also truck or vehicle-carried contraband or explosives, as for instance they proceed through a portal or checkpoint.

Figure 10:
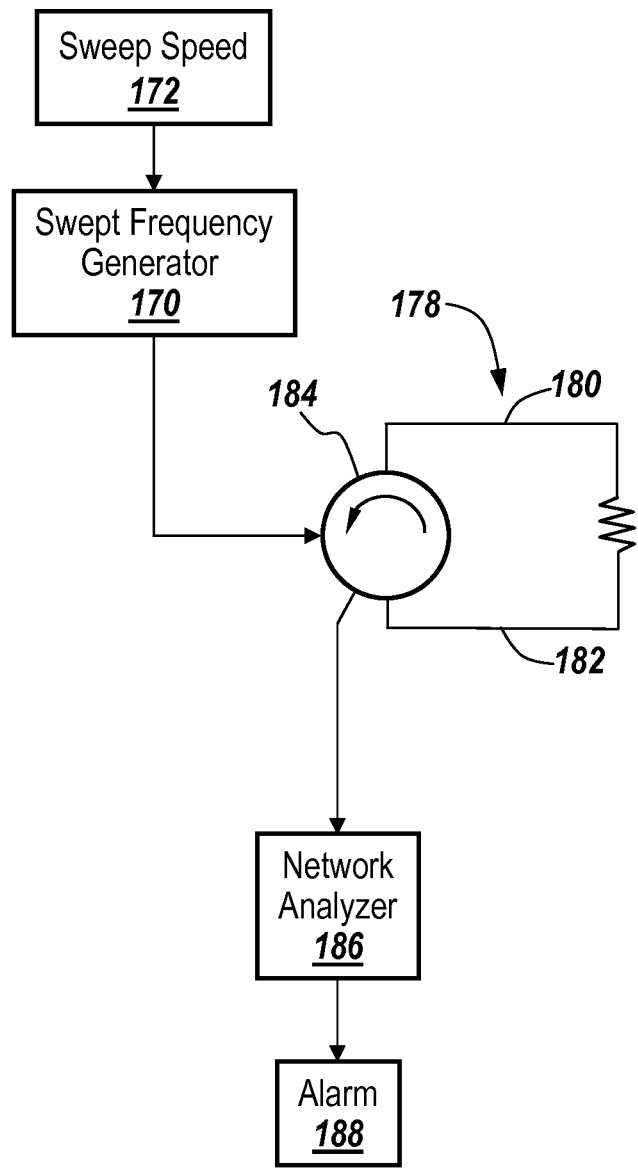
FIG. 10 is a block diagram of a swept frequency generator coupled to a terminated balanced transmission line.

Referring now to FIG. 10, the subject system has been described in terms of swept frequency production. Here a swept frequency CW source 170 is provided with a sweep speed control 172.

Here all swept frequency source 170 is coupled to circulator 184. It is also possible to synthesize swept frequency signals digitally. The output of circulator 184 is applied to a network analyzer or receiver 186 that, inter alia, enables correlations between spectral lines found at the various frequencies to target molecule spectral lines, whereupon signals representative of the presence of the target molecule may be applied to an alarm 188.

Note, that sweep timing is not critical as long as the network analyzer can detect correlations as they occur and output the result of the correlations. This assumes that the sweep is slow enough to provide appropriate dwell time at a spectral line.

The result is the ability to quickly scan spectral lines of target and non-target molecules.

Figure 11:
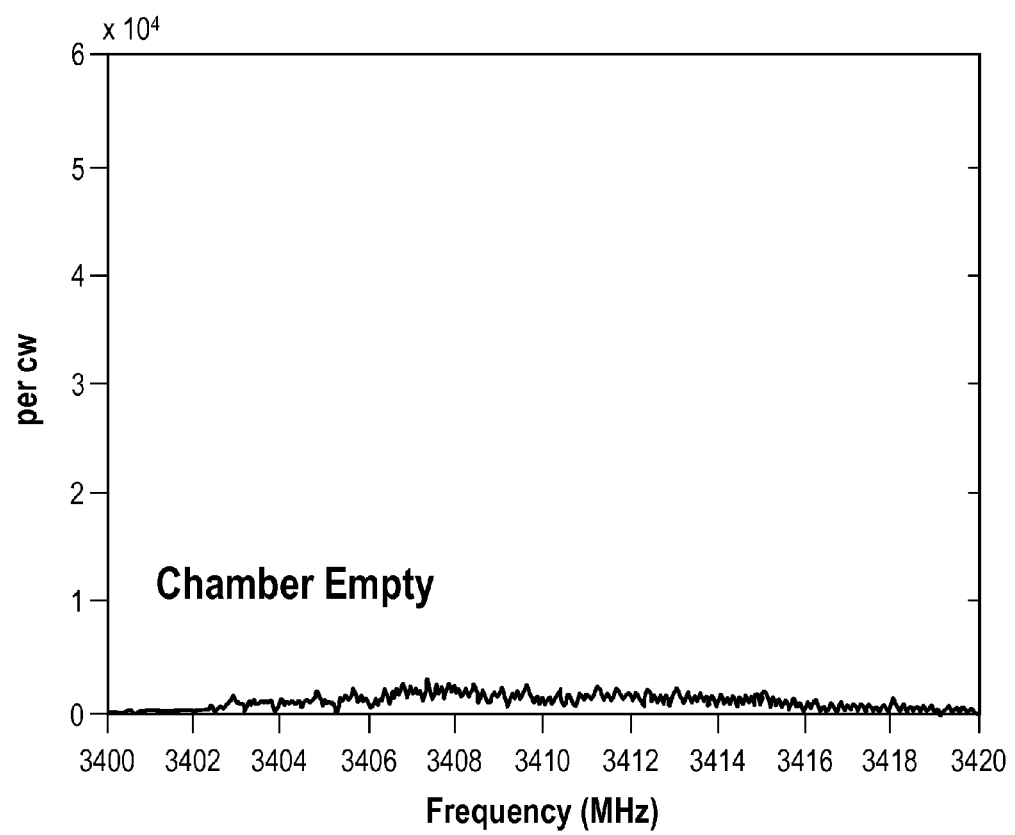
FIG. 11 is a test plot for the subject system monitoring an empty chamber; and, FIG. 12 is a test plot of the detector of RDX resonance using a frequency sweep and 1.7 watts at 74° F.

Referring to FIG. 11, what is shown is a plot of the response of the subject system to an empty chamber showing no resonance peaks.

Figure 12:
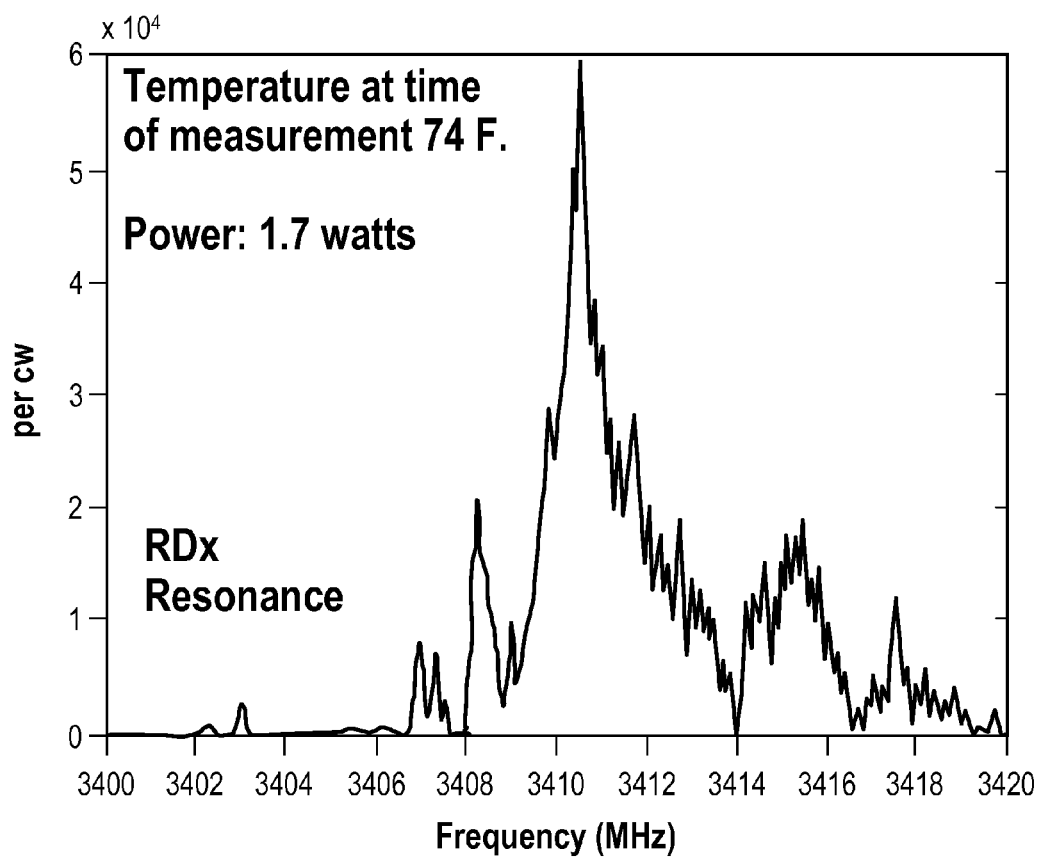

Referring now to FIG. 12, what is shown is a plot of the response of the subject system to the presence of RDX in the chamber, illustrating characteristic RDX peaks, with the input power bay 1.7 watts at a temperature of 74° F.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for performing a nuclear quadrupole resonance measurement on a material, comprising the steps of:
   placing a target material having spectral line associated therewith between the conductors of a balanced non-coiled non-resonant untunable transmission line having parallel spaced apart conductors terminated with a resistive element equal to the impedance of the balanced transmission line;
   driving the transmission line through a circulator with a swept frequency continuous wave signal having a frequency equal to that of one of the spectral lines of the target material to produce a stimulated emission; and,
   detecting the stimulated emission from the target material from an output of the circulator.

2. The method of claim 1, wherein the material includes molecules having a predetermined spectra.

3. The method of claim 2, wherein the frequency at which the balanced transmission line is driven is less than 10 MHz.

4. The method of claim 2, wherein the frequency at which the balanced transmission line is driven below 8 MHz.

5. The method of claim 4, wherein the balanced transmission line is driven above 100 KHz.

6. The method of claim 1, wherein the frequency at which the balanced transmission line is driven is swept from a low frequency to a high frequency.

7. The method of claim 6, wherein the sweeping of the frequency is performed in a continuous fashion.

8. The method of claim 1, wherein the signal that drives the balanced transmission line is coded.

9. The method of claim 8, wherein the code is a PN code.

10. The method of claim 1, and further including a first set of transmission lines laid out side by side with each of the transmission lines being driven by a signal that matches the spectral lines of the target material.

11. The method of claim 10, and further including a second set of transmission lines overlying the first set of transmission lines at an angle so as to provide a grid of transmission lines.

12. The method of claim 11, and further including the step of ascertaining the location of the target material by processing the outputs of the grid.

13. The method of claim 1, wherein the driving step includes driving the transmission line with frequencies matching spectral lines of more than one molecule in the target material, and further including the step of ascertaining from the stimulated emission from the target material the ratio of the components in the target material.

14. The method of claim 1, wherein the balanced transmission line is located at a portal.

15. The method of claim 14, wherein the portal includes one of an access gate, an airline security gate and a border crossing gate.

16. The method of claim 1, wherein the balanced transmission line is incorporated within a shipping container.

17. The method of claim 1, wherein the balanced transmission line surrounds a container.

18. The method of claim 17, wherein the container includes a vehicle.

19. The method of claim 17, wherein the container is a mounted shipboard and includes a transmitter for transmitting the results of the simulated transmission detection.

20. The method of claim 19, wherein the transmitter is part of a mesh network within the ship such that container contents is continuously monitorable by monitoring signals on the mesh network.

21. The method of claim 2, wherein the molecules include an explosive.

22. The method of claim 2, wherein the molecules includes contraband.

23. The method of claim 2, wherein the molecules include at least one drug.

24. The method of claim 23, wherein the drug includes a narcotic.

25. The method of claim 24, wherein the narcotic includes at least one of heroin or cocaine.

26. The method of claim 24, wherein the drug includes pain medication.

27. The method of claim 26, wherein the drug includes Oxycontin.

* * * * *